(12) United States Patent
Feucht et al.

(10) Patent No.: US 8,688,229 B2
(45) Date of Patent: Apr. 1, 2014

(54) ALTERNATING MAGNETIC FIELD APPLICATION DEVICE FOR HEATING MAGNETIC OR MAGNETIZABLE SUBSTANCES IN BIOLOGICAL TISSUE

(75) Inventors: Peter Feucht, Berlin-Lankwitz (DE); Volker Brüss, Berlin (DE); Andreas Jordan, Berlin (DE)

(73) Assignee: Magforce AG, Berlin (DE)

( * ) Notice: Subject to any disclaimer, the term of this patent is extended or adjusted under 35 U.S.C. 154(b) by 486 days.

(21) Appl. No.: 12/934,625
(22) PCT Filed: Mar. 6, 2009
(86) PCT No.: PCT/EP2009/001595
§ 371 (c)(1),
(2), (4) Date: Jan. 20, 2011
(87) PCT Pub. No.: WO2009/118091
PCT Pub. Date: Oct. 1, 2009

(65) Prior Publication Data
US 2011/0160515 A1   Jun. 30, 2011

(30) Foreign Application Priority Data
Mar. 28, 2008  (EP) .................................. 08005951

(51) Int. Cl.
A61F 2/00 (2006.01)
A61F 7/12 (2006.01)
A61N 2/00 (2006.01)

(52) U.S. Cl.
USPC ............................. 607/103; 607/113; 600/10

(58) Field of Classification Search
USPC .............................. 600/10; 607/100, 101, 103
See application file for complete search history.

(56) References Cited

U.S. PATENT DOCUMENTS

| | | |
|---|---|---|
| 4,340,038 A | 7/1982 | McKean |
| 5,147,284 A | 9/1992 | Fedorov et al. |
| 6,575,893 B2 * | 6/2003 | Feucht ............................. 600/13 |
| 2003/0032995 A1 * | 2/2003 | Handy et al. .................. 607/103 |
| 2003/0045770 A1 | 3/2003 | Van Mullekom |
| 2005/0021088 A1 * | 1/2005 | Schuler et al. .................... 607/1 |

FOREIGN PATENT DOCUMENTS

| | | |
|---|---|---|
| DE | 19939001 A1 | 3/2001 |
| EP | 1102609 B1 | 11/2002 |

(Continued)

OTHER PUBLICATIONS

International Search Report in related PCT Application No. PCT/EP2009/001595.

(Continued)

*Primary Examiner* — Linda Dvorak
*Assistant Examiner* — Jared W Pike
(74) *Attorney, Agent, or Firm* — The Marbury Law Group, PLLC

(57) ABSTRACT

The invention relates to an alternating magnetic field application device for heating magnetic or magnetizable substances in biological tissue, in particular for thermal therapy using magnetic nanoparticles, composed of a large applicator (1) having a magnetic yoke (2) and two oppositely situated pole shoes (7, 8) on the magnetic yoke (2) which are separated by an exposure gap (13), and having two magnetic coils (9, 10), which are respectively associated with a pole shoe (7, 8), for generating a substantially homogenous alternating magnetic field (12) of a given field strength in the exposure gap (13), wherein the biological tissue to be irradiated may be brought into the exposure gap (13) as an exposure target volume. According to the invention, in the exposure gap (13) a field concentrator (19) is situated in the immediate proximity of the biological tissue to be irradiated as the exposure target volume, in particular on or in a patient in the immediate proximity of a body part to be irradiated, such as a diseased prostate (23), the field concentrator concentrating the alternating magnetic field (12) of the large applicator (1) in the target volume and thereby locally enhancing the alternating magnetic field at that location.

21 Claims, 8 Drawing Sheets

(56) References Cited

FOREIGN PATENT DOCUMENTS

| JP | 2007-267875 | 10/2007 |
| WO | WO 01/56656 A1 | 8/2001 |

OTHER PUBLICATIONS

Jordan, et al., "Nanoparticles for Thermotherapy", Nanotechnologies for the Life Science, vol. 6, ISBN: 3-527-31386-9, pp. 242-258, (2006).

* cited by examiner

ALTERNATING MAGNETIC FIELD APPLICATION DEVICE FOR HEATING MAGNETIC OR MAGNETIZABLE SUBSTANCES IN BIOLOGICAL TISSUE

The invention relates to an alternating magnetic field application device for heating magnetic or magnetizable substances in biological tissue, in particular for thermal therapy using magnetic nanoparticles, according to the preamble of Claim 1.

A known generic alternating magnetic field application device (EP 1 102 609 B1) is composed of a large applicator having a magnetic yoke and two oppositely situated pole shoes on the magnetic yoke which are separated by an exposure gap, and having two magnetic coils which are respectively associated with a pole shoe. Connected thereto is a large applicator control unit for supplying alternating current having a given amplitude, frequency, and phase position in order to generate a substantially homogeneous alternating magnetic field of a given field strength in the exposure gap. The biological tissue to be irradiated as the exposure target volume is accommodated in the exposure gap. In particular, a patient having a body part to be irradiated as the target volume, for example having a diseased prostate, may be placed in the exposure gap.

The alternating magnetic field application device according to the invention is described and explained below by way of example primarily on the basis of cancer of the prostate, without thus being limited to this application, since other diseases, in particular other tumors in the upper abdominal or pelvic region, may also be correspondingly treated.

The known large applicator has an effective field diameter of the alternating magnetic field of approximately 300 mm, the field strength being settable up to 18 kA/m. A relatively large body surface area is affected in irradiation of tumors in the upper abdominal or pelvic region, in particular cancer of the prostate, of a patient; the irradiation induces large ring currents which may result in excessive heating of skin surfaces, muscle tissue, and bone, for example in the pelvic region, also resulting in uncontrollable nerve stimulation and therefore a significant burden on a patient. Due to these circumstances, for these applications the known large applicator can be operated only at field strengths of approximately 4 to 4.5 kA/m, for which the ring current effects may usually be well tolerated by a patient.

At a maximum dosage of a magnetofluid in a diseased prostate, for irradiation using only the large applicator temperature increases only up to approximately 41° C. or less may be achieved at that location. This is sufficient for sensitizing the tumor in a combination treatment in conjunction with another type of radiation for a positive therapeutic effect. However, for direct destruction of the tumor tissue, a temperature increase to approximately 45° C. or greater would be necessary. Use of a 100-kHz alternating magnetic field would require a field strength of the large applicator of approximately 7 kA/m or greater, which, as stated above, is practically intolerable by a patient on account of the ring current effects during the relatively long irradiation time which is required (up to approximately one hour).

The object of the invention, therefore, is to refine a generic alternating magnetic field application device in such a way that therapeutically adequate irradiation of relatively small exposure target volumes, in particular relatively small body regions, of a patient is possible.

This object is achieved by the features of Claim 1.

According to Claim 1, in the exposure gap of the large applicator and in the immediate proximity of the biological tissue to be irradiated as an exposure target volume, a field concentrator is situated, in particular on or in a patient, in the immediate proximity of a body part to be irradiated, such as a diseased prostate, which concentrates the alternating magnetic field of the large applicator in the target volume and thus locally enhances the alternating magnetic field at that location.

It is thus advantageously possible to irradiate at relatively low magnetic field strengths of the large applicator which do not generate eddy currents and ring current burdens which are intolerable for a patient, while still achieving a sufficiently high field concentration in a relatively small target volume, for example in a diseased prostate, so that direct destruction of tumor tissue at that location may be achieved at approximately 45° C. or greater.

It is also possible to easily and cost-effectively manufacture and use a field concentrator with high operational reliability.

By means of the features of Claim 2, a passive field concentrator in the form of ferrite is proposed. Although the concentration effect and local enhancement of the alternating magnetic field of the large applicator are relatively low when ferrite is used, under certain circumstances they may be sufficient for therapeutic purposes. Such a passive field concentrator in the form of ferrite may be manufactured in a particularly simple and cost-effective manner.

By means of the features of Claim 3, on the other hand, an active field concentrator which has a magnetic coil as an induction coil is proposed which, although it is more costly, results in a stronger field concentration and thus a high local enhancement of the alternating magnetic field of the large applicator. Local enhancement factors of approximately 3 to 4 may thus be achieved for cancer of the prostate, for example. This requires that the at least one magnetic coil of the field concentrator is aligned in the device in such a way that the magnetic axes of the field concentrator and of the large applicator are directed in approximately the same direction, and that the magnetic coil is supplied with a synchronized alternating current which is in phase with and of the same frequency as the alternating current of the large applicator.

For such synchronization, it is proposed in Claim 4 that the large applicator control unit and the field concentrator control unit are joined together or integrated with one another in such a way that, for example, the field concentrator is also directly supplied with power by the large applicator control unit in conjunction with a power unit. However, for such a direct coupling the amplitudes of the alternating currents are preferably independently adjustable for the large applicator and the field concentrator, since in particular the maximum allowable amplitude for the applicator is a function of the individual physiological characteristics of a patient, and is different.

Alternatively, for synchronization it is proposed according to Claim 5 that the field concentrator control unit and the large applicator control unit are separate from one another and are operated independently. A sensor which detects the frequency position and phase position of the large applicator alternating magnetic field cooperates with the field concentrator control unit. The resulting values are then processed in the field concentrator control unit for synchronization.

In one particularly preferred refinement according to Claim 6, the magnetic coil of the active field concentrator is designed as a flat coil, wherein the target volume to be irradiated is to be situated approximately perpendicular to the plane of the flat coil in the region of the magnetic axis. In contrast, a cylindrical coil is less suitable for an active field concentrator.

For irradiation of a tumor in the upper abdominal or pelvic region, in particular cancer of the prostate, according to Claim 7 the immediate proximity to the target volume is provided by designing the field concentrator as a rectal applicator having a flat, oblong housing with a configuration and size which conforms to the rectum of a patient as an accommodating space. Such an oblong housing is used as a covering for an elongated flat coil as a magnetic coil, so that the magnetic axis thereof extends approximately perpendicular to the plane of the housing. Such an elongated flat coil may be obtained by winding a circular flat coil, and then compressing it into an elongated shape and optionally also slightly bending it.

According to Claim 8, at one longitudinal end of the housing a tubular insertion piece is connected to the housing, and depending on the anatomical circumstances is angled with respect to the plane of the housing. The rectal applicator together with this insertion piece may be inserted into the rectum and thus adjusted and fixed in position as needed. Due to anatomical requirements, according to Claim 9 the housing is approximately 65 mm to 70 mm long, 20 mm high, and 35 mm wide, with an approximately oval cross section and rounded edges. The surface area in the field direction should be as large as possible. The larger this surface area, the greater the usable range of the magnetic field which is emitted by the magnetic coil in the direction of the field. The insertion piece has a diameter of approximately 10 mm, which is smaller than that of the housing, since when the rectal applicator is used the pipe socket remains in the region of the sphincter muscle, thus reducing irritation at that location on account of its small diameter. In addition, according to Claim 10 the aim is to improve tolerability by the fact that, although the housing and the insertion piece are produced in a dimensionally stable form, at least the housing has a covering made of a soft material.

According to Claim 11, in one advantageous specific embodiment the electrical connecting lines to the magnetic coil as well as a coolant inlet and a coolant outlet are connected to the insertion piece, and/or are led through same into the housing. The magnetic coil in the housing as well as the connecting lines are cooled by the coolant.

According to Claim 12, in a continuation the electrical connecting lines and coolant tubes are accommodated, with the smallest possible cross section, in a flexible connecting tube mounted on the insertion piece. It is important that during the relatively long irradiation time period the smallest possible transverse forces, which reduce tolerability and could result in an unfavorable maladjustment with regard to the field direction of the large applicator, act on the insertion piece due to the flexible connecting tube together with the flexible connecting lines.

In one advantageous design according to Claim 13, the electrical connecting lines and a coolant inlet tube are led inside the connecting tube and the insertion piece, the remaining cross section of the connecting tube or of the insertion piece being used for coolant return. A simple configuration in addition to effective cooling of the electrical connecting lines, which are guided in the return flow, is thus achieved.

Claim 14 states setting values which have been successfully tested in a clinical setting, such that a field strength of approximately 3 kA/m to 4 kA/m is set at the large applicator; in conjunction with the present rectal applicator in particular, a 3- to 4-fold increase in field strength in the target volume, in particular for cancer of the prostate, may be achieved.

According to Claim 15, the treatment is periodically carried out in a large applicator in conjunction with the active field concentrator, in particular as a rectal applicator, with simultaneous activation of both applicators. Depending on the circumstances, a time-delayed activation, optionally in combination with subsequent simultaneous activation of the individual applicators, may also result in therapeutic success. If needed, separate use of the rectal applicator, independently of a large applicator, is possible for therapy, in particular when a treatment area is located only approximately 10 to 20 mm from the intestinal wall of the rectum. Such a use also requires protection; for the rectal applicator a separate unit is also required for protection.

For the treatment of a patient in the large applicator, a substantially homogeneous magnetic field is basically present in the abdomen, directed from the stomach area toward the back, wherein an inserted rectal applicator has the function of the active field concentrator in the region of the intestine and prostate. However, due to the human anatomy as dictated by the orientation of the rectum, the magnetic field axis of the rectal applicator is slightly inclined relative to the magnetic field axis of the large applicator in the direction of the head, so that the required accurate, equal orientation of the two magnetic field axes in conjunction with a rectal applicator is not possible. Thus, although the function of the rectal applicator as a field concentrator for field enhancement in a diseased prostate is reduced, for a mutual inclination of the field axes by approximately 20° to 30° a resulting loss of field strength, compared to a maximum enhancement of 6% to 14%, is adequate and acceptable for the therapy.

When the rectal applicator is used, there is the fundamental problem that its magnetic coil is relatively small, and its magnetic field decreases by a power of three with increasing distance. Efforts should therefore be made to make the maximum possible use of the field strength of the large applicator by setting its field strength to be as high as possible. However, as previously stated, a high field strength setting on the large applicator results in undesired heating over the patient's entire body due to the ring currents induced in the patient as a function of the irradiated areas. This is a particular problem for corpulent patients. As a result of corpulence, the problem is worsened due to the fact that the exposure gap on the large applicator must be set wide, thus further increasing the undesired ring currents in the patient. Therefore, it is proposed in Claim 16 that, in particular for corpulent patients, directly at the surface above and/or below a patient the alternating magnetic field is prefocused using further, appropriately situated flat induction coils which are correspondingly excited at a synchronous frequency and phase.

The invention is further explained with respect to the drawings, which show the following:

Figure 4:
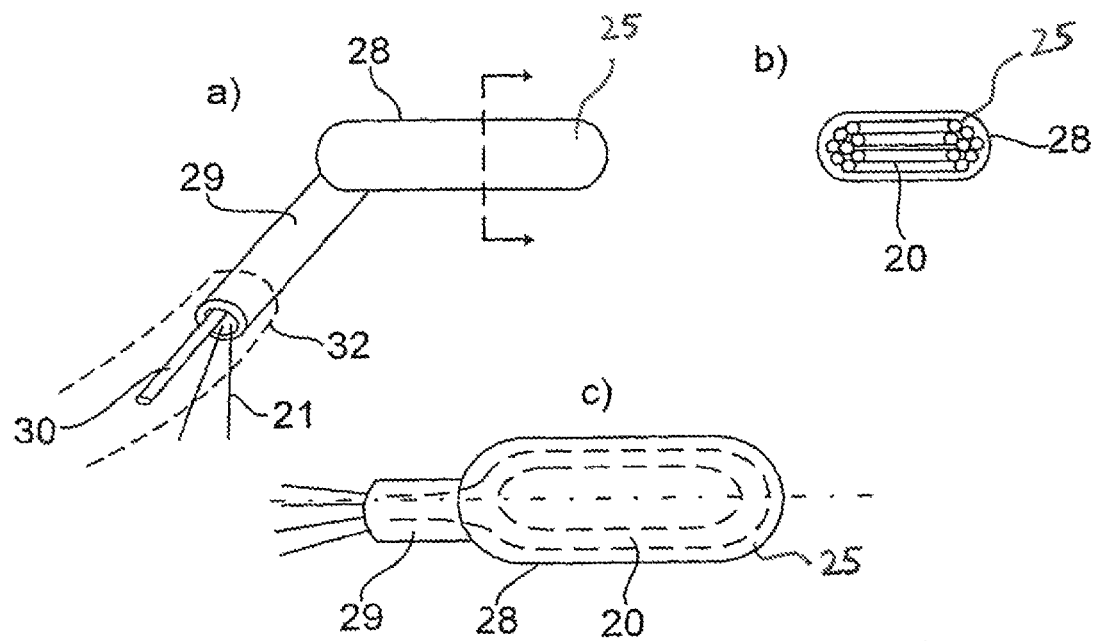
Figure 5:
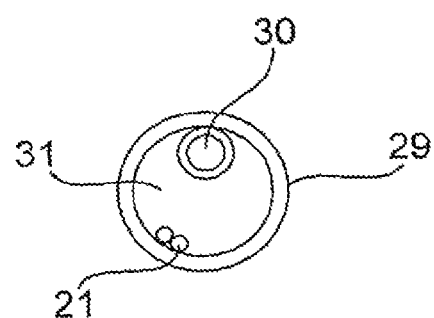
Figure 6:
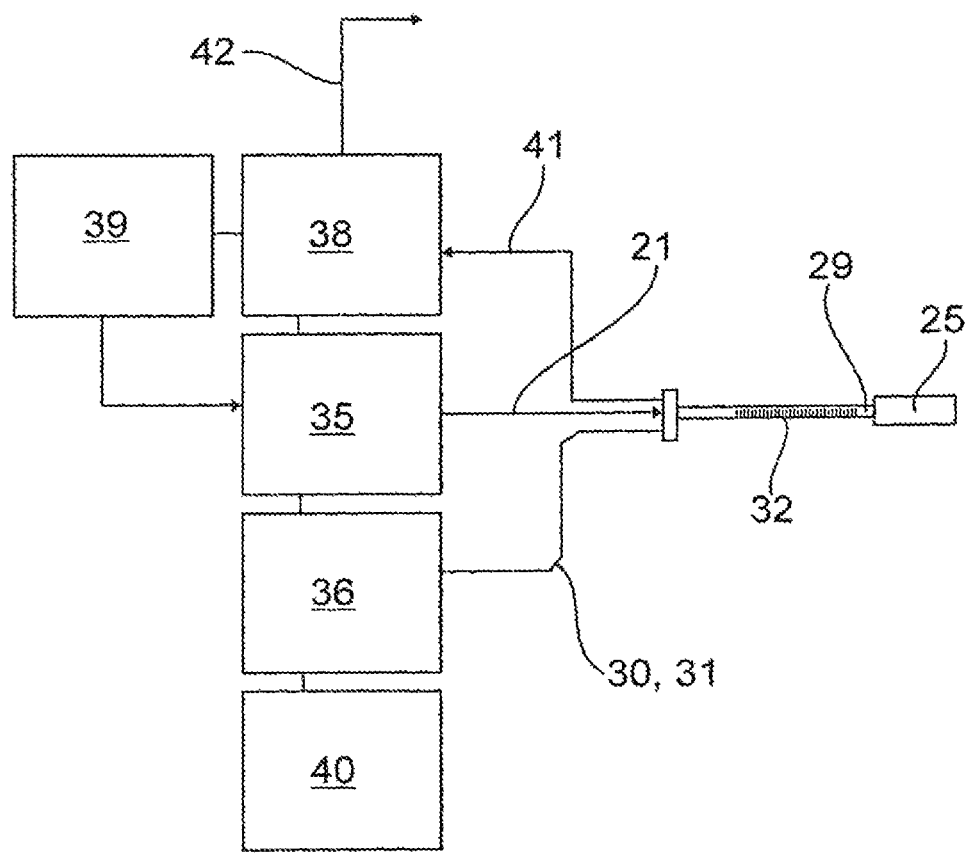

FIGS. 4a, b, c show various views of a rectal applicator;

FIG. 5 shows a cross section of the insertion piece of the rectal applicator according to FIG. 4; and FIG. 6 shows a block diagram of the control and power electronics systems of the rectal applicator.

Figure 7A:
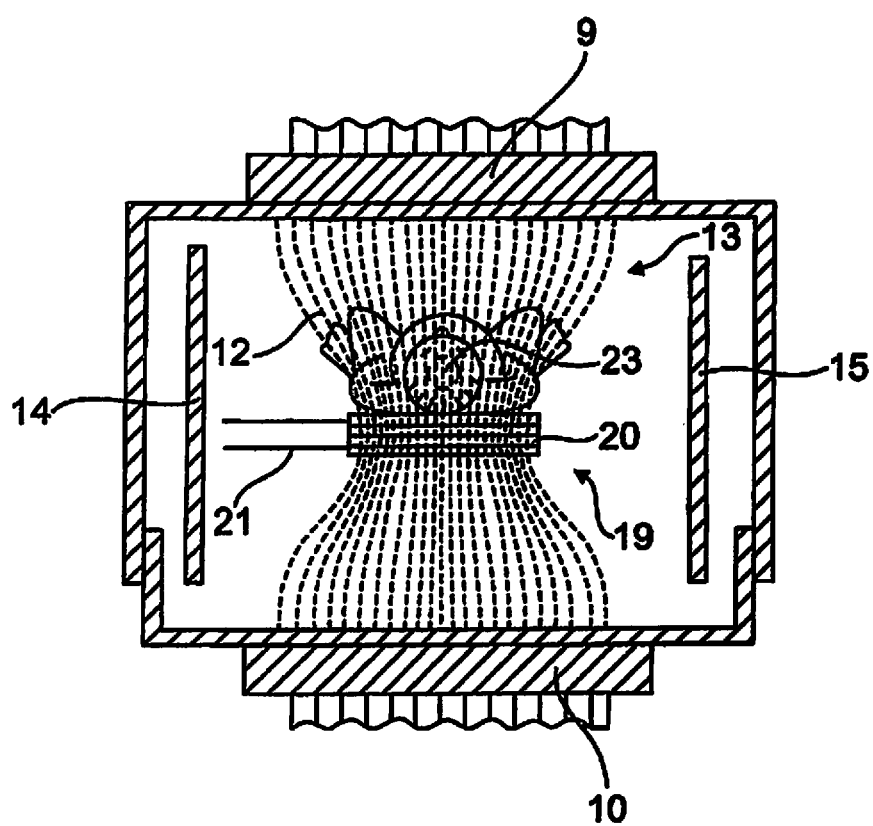

FIG. 7a shows a flat induction coil below a patient.

Figure 7B:
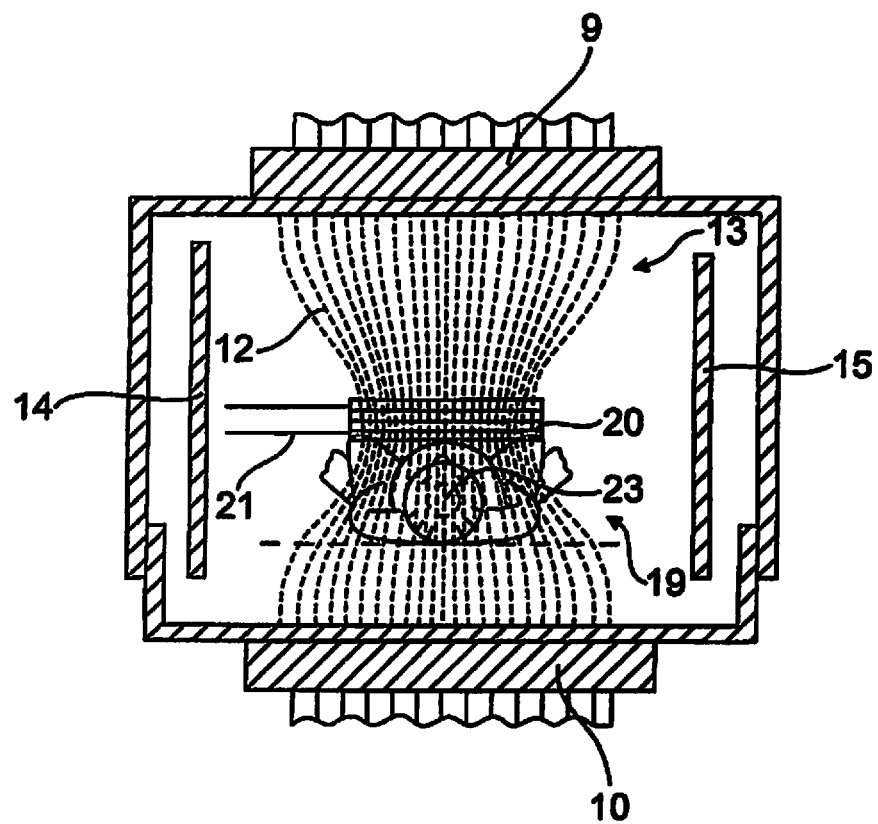

FIG. 7b shows a flat induction coil above a patient.

Figure 7C:
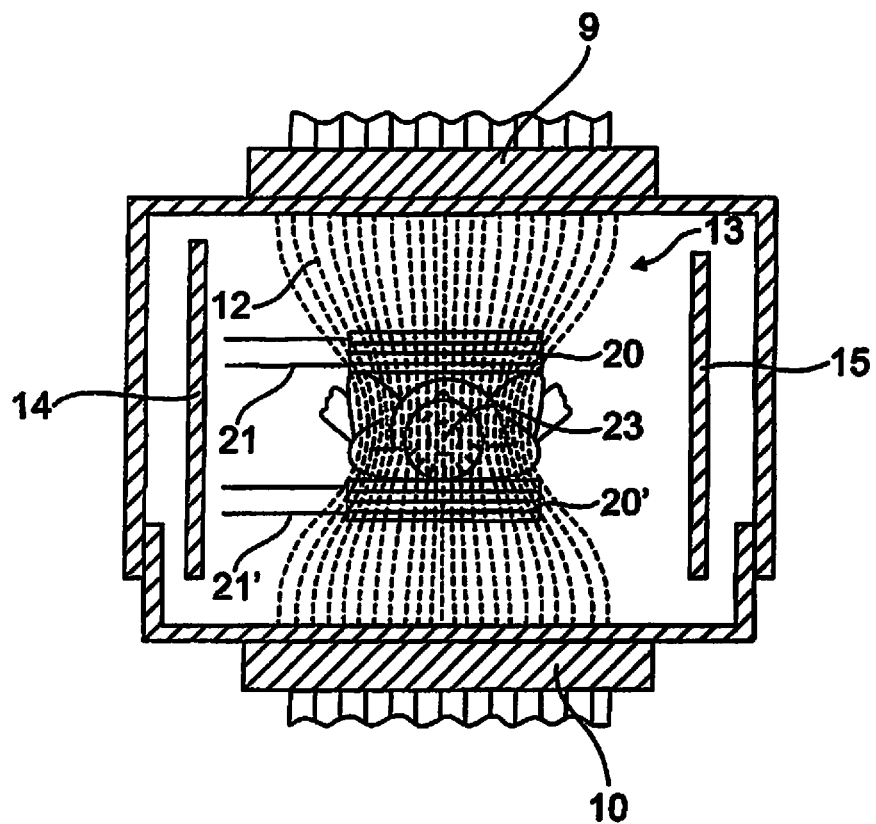

FIG. 7c shows flat induction coils below and above a patient.

Figure 1:
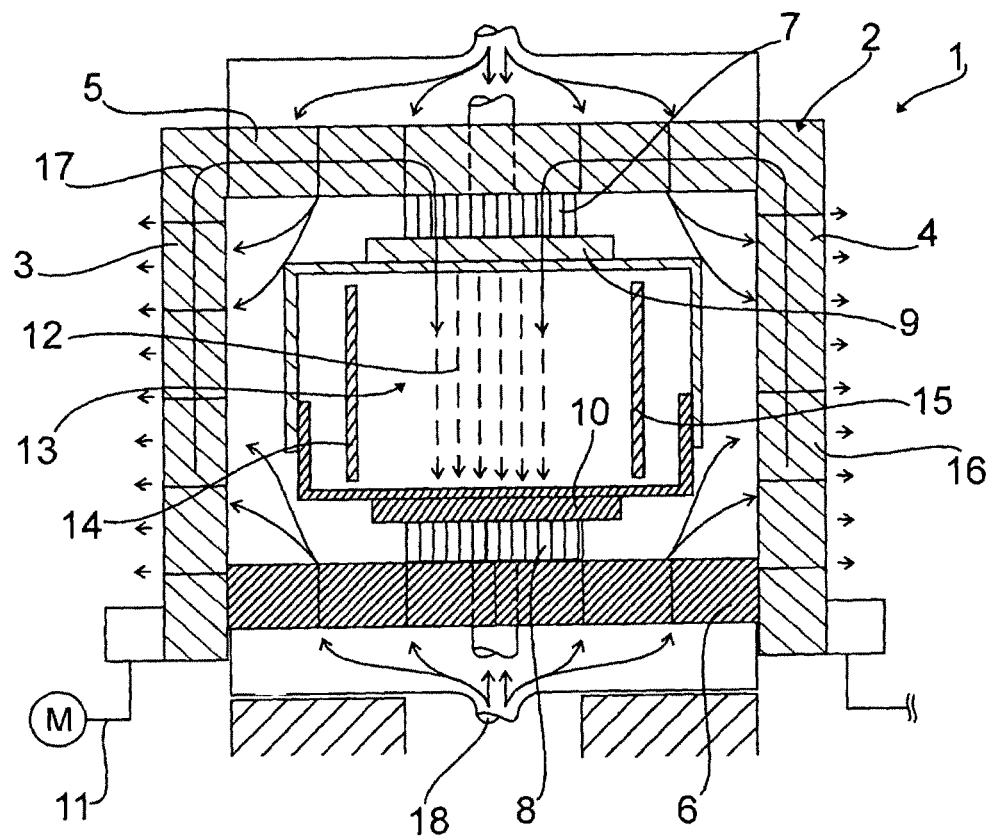
FIG. 1 shows a schematic sectional view of a magnetic field applicator as a large applicator.

FIG. 1 schematically illustrates a magnetic field applicator as a large applicator 1 for thermal therapy or hyperthermia, in which a body, into which a magnetic or magnetizable substance is introduced as a magnetofluid, may be irradiated.

The large applicator 1 includes a magnetic yoke 2 designed as a three-legged system having an M shape, two interspaced parallel vertical yoke sections 3, 4, and two transverse yoke sections 5, 6 connected therebetween.

An assembly composed of a lower transverse yoke section 6 and a lower pole shoe 8 associated therewith, together with a lower magnetic coil 10, is stationarily mounted. A gate composed of the two vertical yoke sections 3, 4, the connected upper transverse yoke section 5, and the upper pole shoe 7 together with an upper magnetic coil 9 associated therewith may be displaced with respect to the assembly by means of a self-locking spindle drive 11, schematically illustrated here, for setting the exposure gap width of the exposure gap 13. A substantially homogeneous alternating magnetic field 12 having a field strength which is tolerable for a patient (up to approximately 4 kA/m for the use explained below) may be generated in the exposure gap 13.

The exposure gap 13 is delimited by partitions 14, 15 which border an insertion space for a patient.

The upper magnetic coil 9 and the lower magnetic coil 10 are designed as disc coils having one or more windings, made of stranded copper wires, which extend in a spiral fashion.

The magnetic yoke 2 and the pole shoes 7, 8 are composed of ferrite modules 16 having gaps therebetween. A cooling housing having recesses 18 is provided on the large applicator 1, through which the cooling air is introduced and which exits through gaps on the magnetic yoke. The ferrite modules 16 are made of successively arranged ferrite plates which are oriented in the magnetic yoke 2 along the magnetic flow direction 17, and which are separated from one another, transverse to the magnetic flow direction 17, by the cooling gaps.

Figure 2:
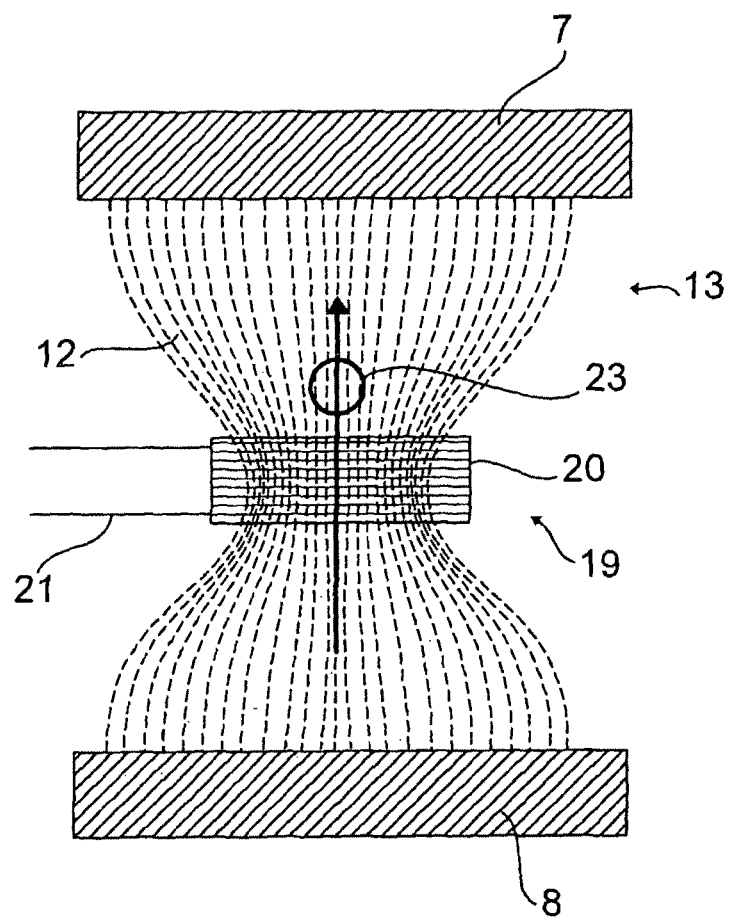
FIG. 2 shows a schematic illustration of an alternating magnetic field of the large applicator together with a field concentrator.

FIG. 2 schematically illustrates the region of the exposure gap 13 between the pole shoes 7, 8 of the large applicator, having an active field concentrator 19 mounted therein. The field concentrator 19 is composed of a flat coil 20 having connecting lines 21; the magnetic axis of the large applicator and the magnetic axis of the flat coil 20 are oriented in the same direction and coincide. In addition, the flat coil 20 is supplied with a synchronized alternating current which is in phase with and of the same frequency as the alternating current of the large applicator 1. This results in the illustrated function of an active field concentrator 19 having field enhancement in the region of the flat coil 20. In the immediate proximity of the flat coil 20 a schematically illustrated body part to be irradiated, a pathologically enlarged prostate 23, for example, is supported as a target volume; it is apparent that concentration and local enhancement of the alternating magnetic field of the large applicator are achieved using the field concentrator 19.

Figure 3:
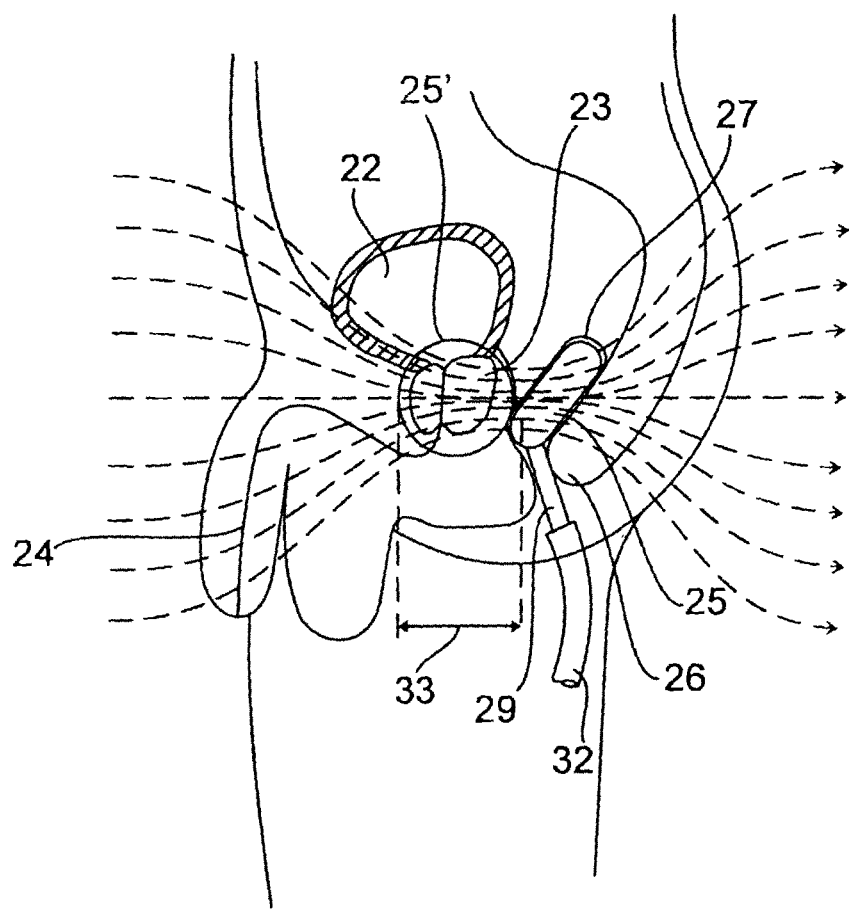
FIG. 3 shows a schematic illustration of a patient with cancer of the prostate, with the rectal applicator inserted.

The system according to FIG. 2 is shown in a more specific manner in FIG. 3, in which a pathologically enlarged prostate 23 is correspondingly irradiated. For this purpose, a schematic section through a patient in the region of the lower abdomen is shown, including a bladder 22 and the prostate 23, situated at the lower outlet of the bladder, which annularly encloses the urethra 24. In this case the region of the prostate is the target volume for the irradiation, and its position and size are indicated by a circle 25'. In the present case, a rectal applicator 25 as the active field concentrator 19 is inserted past the sphincter muscle 26 and into the rectum 27. The rectal applicator 25 is explained in greater detail with reference to FIGS. 4 and 5:

FIG. 4a shows a side view, FIG. 4b shows a cross section, and FIG. 4c shows a top view of the rectal applicator 25. The rectal applicator 25 contains an oblong flat coil 20 which is enclosed by a housing 28. The housing is approximately 70 mm long, 20 mm high, and 35 mm wide, with an approximately oval cross section and rounded edges, wherein these dimensions correspond to the accommodating volume of the rectum 27. As shown in FIG. 3, a tubular insertion piece 29 is integrally molded onto one longitudinal end of the housing and angled with respect to the plane of the housing, and lies at an angle with respect to the plane of the housing, depending on the anatomical circumstances. The housing 28 may also have a covering made of a soft material.

As shown in particular in the cross section of the insertion piece 29 according to FIG. 5, the electrical connecting lines 21 and a coolant inlet tube 30 are guided inside the insertion piece 29 and connected, the remaining cross section 31 being used for coolant return. The dimensionally stable insertion piece 29 is connected to a flexible connecting tube 22, through which the electrical connecting lines 21 and the coolant inlet tube 30 are led.

It is apparent from FIG. 3 that in its function as an active field concentrator, the effective range of the rectal applicator 25 must include the prostate region, corresponding to a range of approximately 70 mm as indicated by double arrow 33. It is also apparent from FIG. 3 that, due to the anatomical position of the rectum 27, the magnetic axis of the flat coil 20 in the rectal applicator 25 is upwardly inclined by an angle with respect to the magnetic axis of the large applicator (shown here extending horizontally). The field concentrator effect of the rectal applicator is thus slightly reduced compared to the ideal case of magnetic axes oriented in the same direction; however, the concentrator effect is sufficient and acceptable.

FIG. 6 illustrates a block diagram 34 for powering and controlling the rectal applicator 25. Specifically, connected to the insertion piece 29 is a connecting tube 32 having a graduated scale for adjusting the insertion, through which the electrical connecting lines 21 from a power amplifier 35 as well as the coolant inlet and outlet 30, 31, which originate from a continuous thermostat 36, are led. Also provided is a control unit 38 which cooperates with an operator station 39, in particular for power adjustment. A monitoring unit 40 is also provided. A signal line 41 which is connected to sensors in the region of the rectal applicator 25 may be led from the rectal applicator 25 back to the control unit. These may be one or more sensors which detect a position, or which for synchronization detect the frequency and phase of the alternating magnetic field of the large applicator and send this information to the control unit 38 for comparison. However, for such synchronization the control unit 38 may also be connected to a control unit of the large applicator, as schematically indicated by line 42.

The invention claimed is:

1. An alternating magnetic field application device for heating magnetic or magnetizable substances in a biological tissue, comprising
  a large applicator, comprising a magnetic yoke and two oppositely situated first and second pole shoes on the magnetic yoke wherein the first and second pole shoes are separated by an exposure gap wherein first and second magnetic coils are respectively associated with the first and second pole shoes,
  with a large applicator control unit connected to the large applicator and configured for supplying alternating current having a given amplitude, frequency, and phase position in order to generate a substantially homogenous alternating magnetic field of a given field strength in the exposure gap, wherein the biological tissue to be exposed to the magnetic field may be brought into the exposure gap as an exposure target volume, wherein a field concentrator located in the exposure gap is situated in the immediate proximity of the biological tissue to be exposed to the magnetic field as the exposure target volume the field concentrator concentrating the alternating magnetic field of the large applicator in the target volume and thereby locally enhancing the alternating magnetic field at the immediate proximity of the biological tissue, wherein the field concentrator is in the form of an active field concentrator and includes at least one magnetic coil, wherein the at least one magnetic coil is aligned in such a way that the field lines of the active field concentrator and of the large applicator are directed in approximately the same direction, and a field concentrator control unit is provided, by means of which the at least one magnetic coil is supplied with a synchronized alternating current which is in phase with and of the same frequency as the alternating current of the large applicator.

2. Alternating magnetic field application device according to claim 1, wherein for synchronization of the frequency and phase position, the large applicator control unit and the field concentrator control unit are joined together or integrated with one another.

3. The alternating magnetic field application device of claim 2, wherein the amplitudes of the alternating currents are independently adjustable for the large applicator and the field concentrator.

4. Alternating magnetic field application device according to claim 1, wherein the field concentrator control unit, as a unit which is independent from the large applicator control unit, has at least one sensor for detection and for synchronization of the frequency and phase position with the alternating magnetic field of the large applicator.

5. Alternating magnetic field application device of claim 1, wherein the at least one magnetic coil of the active field concentrator is a flat coil.

6. Alternating magnetic field application device of claim 1, wherein the active field concentrator is designed as a rectal applicator, having a flat, oblong housing with a configuration and size which conforms to the rectum of the patient as an accommodating space, and a correspondingly elongated flat coil as a magnetic coil is contained in the housing, so that the field direction of the flat coil extends approximately perpendicular to a plane of the housing defined by the length and width of the housing.

7. Alternating magnetic field application device according to claim 6, wherein at one longitudinal end of the housing a tubular insertion piece is connected to the housing and is angled with respect to the plane of the housing, wherein the rectal applicator together with the insertion piece may be inserted into the rectum of the patient and thus adjusted and fixed in position.

8. Alternating magnetic field application device according to claim 7, wherein the housing is approximately 65 mm to 70 mm long, approximately 20 mm high, and approximately 35 mm wide, with an approximately oval cross section and rounded edges, and the insertion piece has a diameter of approximately 10 mm, which is smaller than that of the housing, and a length of approximately 70 mm to 100 mm.

9. Alternating magnetic field application device according to claim 8, wherein the housing and the insertion piece are produced in a dimensionally stable form, and at least the housing has a covering made of a soft material which conforms to the inner wall of the rectum.

10. Alternating magnetic field application device of claim 7, wherein electrical lines connecting to the magnetic coil as well as a coolant inlet and a coolant outlet are connected to the insertion piece, or are led through the insertion piece into the housing.

11. Alternating magnetic field application device according to claim 10, wherein the electrical lines and coolant inlet have a small cross section, and are accommodated in a flexible connecting tube mounted on the insertion piece.

12. Alternating magnetic field application device according to claim 11, wherein the electrical lines and a coolant tube connecting to the coolant inlet are led inside the connecting tube and the insertion piece, and the cross section remaining from the coolant inlet and the electrical lines is used for coolant return.

13. Alternating magnetic field application device of claim 7, wherein electrical lines connecting to the magnetic coil as well as a coolant inlet and a coolant outlet are connected to the insertion piece, and are led through the insertion piece into the housing.

14. Alternating magnetic field application device according to claim 13, wherein the electrical lines and coolant inlet have a small cross section, and are accommodated in a flexible connecting tube mounted on the insertion piece.

15. Alternating magnetic field application device according to claim 14, wherein the electrical lines and a coolant tube connecting to the coolant inlet are led inside the connecting tube and the insertion piece, and the cross section remaining from the coolant inlet and the electrical lines is used for coolant return.

16. Alternating magnetic field application device of claim 1, wherein the field strength of approximately 3 kA/m to 4 kA/m is set on the large applicator, and by means of the active field concentrator an approximately 3- to 4-fold increase in field strength in the target volume is achieved.

17. Alternating magnetic field application device of claim 1, wherein the active field concentrator, may be activated and used simultaneously or partially simultaneously with the large applicator, or independently and separately from the large applicator.

18. Alternating magnetic field application device of claim 1, wherein directly at the surface above or below the patient the alternating magnetic field is pre-focused using further flat induction coils situated at the surface above or below the patient, wherein the pre-focused alternating magnetic field is correspondingly excited at a frequency and phase which are synchronous with the alternating magnetic field of the large applicator.

19. The alternating magnetic field application device of claim 1, wherein the biological tissue is a body part of a patient.

20. The alternating magnetic field application device of claim 19, wherein the body part is a diseased prostate.

21. Alternating magnetic field application device of claim 1, wherein directly at the surface above and below the patient the alternating magnetic field is pre-focused using further flat induction coils situated at the surface above and below the patient, wherein the pre-focused alternating magnetic field is correspondingly excited at a frequency and phase which are synchronous with the alternating magnetic field of the large applicator.

* * * * *